(12) United States Patent
Ahn

(10) Patent No.: US 9,474,624 B1
(45) Date of Patent: Oct. 25, 2016

(54) INTERVERTEBRAL FUSION CAGE

(71) Applicant: AEGIS SPINE, INC., Greenwood Village, CO (US)

(72) Inventor: Young-Bo Ahn, Greenwood Village, CO (US)

(73) Assignee: AEGIS SPINE, INC., Greenwood Village, CO (US)

( * ) Notice: Subject to any disclaimer, the term of this patent is extended or adjusted under 35 U.S.C. 154(b) by 0 days.

(21) Appl. No.: 14/698,295

(22) Filed: Apr. 28, 2015

(51) Int. Cl.
*A61F 2/44* (2006.01)

(52) U.S. Cl.
CPC ............. *A61F 2/4455* (2013.01); *A61F 2/442* (2013.01); *A61F 2230/0086* (2013.01)

(58) Field of Classification Search
CPC ........ A61F 2/44; A61F 2/4455; A61F 2/447; A61F 2/4611
USPC .................................. 623/17.11, 17.15–17.16
See application file for complete search history.

(56) References Cited

U.S. PATENT DOCUMENTS

| | | | | |
|---|---|---|---|---|
| 6,143,032 | A * | 11/2000 | Schafer et al. ............ | 623/17.11 |
| 6,143,033 | A * | 11/2000 | Paul et al. ................. | 623/17.11 |
| 6,451,057 | B1 * | 9/2002 | Chen et al. ................ | 623/17.15 |
| 6,458,159 | B1 * | 10/2002 | Thalgott .................... | 623/17.11 |
| 6,482,233 | B1 * | 11/2002 | Aebi et al. ................. | 623/17.11 |
| 6,676,703 | B2 * | 1/2004 | Biscup ....................... | 623/17.16 |
| 8,221,502 | B2 * | 7/2012 | Branch, Jr. ................ | 623/17.15 |
| 8,287,597 | B1 * | 10/2012 | Pimenta et al. ........... | 623/17.16 |
| 8,906,095 | B2 * | 12/2014 | Christensen et al. ...... | 623/17.15 |
| 9,211,194 | B2 * | 12/2015 | Bagga et al. | |
| 9,216,096 | B2 * | 12/2015 | Lynn et al. | |
| 2002/0068976 | A1 * | 6/2002 | Jackson .................... | 623/17.15 |
| 2002/0068977 | A1 * | 6/2002 | Jackson .................... | 623/17.15 |
| 2003/0004576 | A1 * | 1/2003 | Thalgott ................... | 623/17.16 |
| 2003/0023312 | A1 * | 1/2003 | Thalgott ................... | 623/17.16 |
| 2003/0105527 | A1 * | 6/2003 | Bresina ..................... | 623/17.16 |
| 2003/0109928 | A1 * | 6/2003 | Pasquet et al. ........... | 623/17.11 |
| 2003/0114931 | A1 * | 6/2003 | Lee et al. .................. | 623/17.11 |
| 2003/0130737 | A1 * | 7/2003 | McGahan et al. ........ | 623/17.11 |
| 2004/0172130 | A1 * | 9/2004 | Nakahara et al. ........ | 623/17.11 |
| 2005/0071005 | A1 * | 3/2005 | Carli et al. ................ | 623/17.11 |
| 2005/0143822 | A1 * | 6/2005 | Paul .......................... | 623/17.16 |
| 2006/0058876 | A1 * | 3/2006 | McKinley ................. | 623/17.11 |
| 2006/0100705 | A1 * | 5/2006 | Puno et al. ................ | 623/17.11 |
| 2007/0027544 | A1 * | 2/2007 | McCord et al. ........... | 623/17.11 |
| 2007/0050031 | A1 * | 3/2007 | Khosrowshahi ........... | 623/17.11 |
| 2007/0162129 | A1 * | 7/2007 | Edie et al. ................. | 623/17.11 |

(Continued)

FOREIGN PATENT DOCUMENTS

| | | |
|---|---|---|
| KR | 10-2011-0013651 A | 2/2011 |
| KR | 10-2014-0018668 A | 2/2014 |

*Primary Examiner* — Eduardo C Robert
*Assistant Examiner* — Michelle C Eckman
(74) *Attorney, Agent, or Firm* — Baker & Hostetler LLP

(57) ABSTRACT

Disclosed is an intervertebral fusion cage which may be inserted between vertebrae from which a disk is removed to restore and maintain an interval between two vertebrae, and more specifically, to an intervertebral fusion cage having an easily mountable shape while enlarging a contact area with blood in a spinal cavity during surgery. A intervertebral fusion cage 100 generally includes a front part 102, first and second side parts 106 and 108 connected to both ends of the front part 102, and a rear part 104 connected to the pair of first and second side parts 106 and 108, wherein the front part 102, the first and second side parts 106 and 108 and the rear part 104 define fixing holes 130 and 132 therein which are vertically opened.

5 Claims, 7 Drawing Sheets

(56) References Cited

U.S. PATENT DOCUMENTS

| | | | |
|---|---|---|---|
| 2008/0221695 A1* | 9/2008 | Jacofsky et al. | 623/17.16 |
| 2008/0243252 A1* | 10/2008 | Hansen et al. | 623/17.16 |
| 2008/0275506 A1* | 11/2008 | Baynham et al. | 606/261 |
| 2008/0306598 A1* | 12/2008 | Hansen et al. | 623/17.16 |
| 2009/0030520 A1* | 1/2009 | Biedermann et al. | 623/17.16 |
| 2009/0149957 A1* | 6/2009 | Burd et al. | 623/17.16 |
| 2010/0152853 A1* | 6/2010 | Kirschman | 623/17.11 |
| 2010/0168798 A1* | 7/2010 | Clineff et al. | 606/279 |
| 2010/0234956 A1* | 9/2010 | Attia et al. | 623/17.16 |
| 2010/0262245 A1* | 10/2010 | Alfaro et al. | 623/17.16 |
| 2011/0040382 A1* | 2/2011 | Muhanna | 623/17.11 |
| 2011/0106259 A1* | 5/2011 | Lindenmann et al. | 623/17.16 |
| 2011/0106261 A1* | 5/2011 | Chin et al. | 623/17.16 |
| 2011/0166660 A1* | 7/2011 | Laurence | 623/17.16 |
| 2011/0172775 A1* | 7/2011 | Flickinger et al. | 623/17.16 |
| 2011/0230970 A1* | 9/2011 | Lynn et al. | 623/17.16 |
| 2012/0010717 A1 | 1/2012 | Spann | |
| 2012/0078370 A1* | 3/2012 | James et al. | 623/17.16 |
| 2012/0095559 A1* | 4/2012 | Woods et al. | 623/17.11 |
| 2012/0158062 A1* | 6/2012 | Nunley et al. | 606/249 |
| 2012/0158143 A1* | 6/2012 | Shapiro | 623/17.16 |
| 2012/0185047 A1* | 7/2012 | Wooley | 623/17.16 |
| 2012/0232664 A1* | 9/2012 | Ulrich et al. | 623/17.16 |
| 2012/0239151 A1* | 9/2012 | Ulrich et al. | 623/17.16 |
| 2013/0006363 A1* | 1/2013 | Ullrich et al. | 623/17.16 |
| 2013/0096683 A1* | 4/2013 | Kube, II | 623/17.16 |
| 2014/0277485 A1* | 9/2014 | Johnson et al. | 623/17.16 |
| 2014/0330383 A1* | 11/2014 | Wimberley et al. | 623/17.16 |
| 2015/0018958 A1* | 1/2015 | Ullrich et al. | 623/17.16 |
| 2015/0100126 A1* | 4/2015 | Melkent et al. | 623/17.16 |
| 2015/0100129 A1* | 4/2015 | Waugh et al. | 623/17.16 |
| 2015/0182347 A1* | 7/2015 | Robinson | A61F 2/447 |
| 2015/0238324 A1* | 8/2015 | Nebosky et al. | A61F 2/447 |
| 2015/0282941 A1* | 10/2015 | Chokshi | A61F 2/447 |
| 2015/0305881 A1* | 10/2015 | Bal et al. | A61F 2/442 |

* cited by examiner

INTERVERTEBRAL FUSION CAGE

BACKGROUND OF THE INVENTION

1. Field of the Invention

The present invention relates to an intervertebral fusion cage which may be inserted between vertebrae from which a disk is removed to restore and maintain an interval between two vertebrae, and more specifically, to an intervertebral fusion cage having an easily mountable shape while enlarging a contact area with blood in a spinal cavity during surgery.

2. Description of the Related Art

A vertebral body includes 32 to 35 vertebrae forming a body, and intervertebral disks, i.e., spinal disks arranged between the vertebrae, and is a portion forming a backbone of a human body that connects an upper skull and a lower pelvis to form the pillar of the truncus. The spine includes 7 cervical vertebrae, 12 thoracic vertebrae, 5 lumbar vertebrae, 5 sacra, and 3 to 5 coccyges from the top. In the case of an adult, 5 sacra are fused together to form one sacral vertebra, and 3 to 5 coccyges are fused together to form one tailbone.

When the intervertebral disc is deteriorated, a prosthesis referred to as an intervertebral cage is used for restoring a distance between two adjacent vertebrae. The intervertebral cage fuses such vertebrae so as not to be moved relative to each other through the growth of a bone graft inserted into the intervertebral cage, in an intervertebral cavity.

Spondylolisthesis refers to a state in which the fourth and fifth lumbar vertebrae are completely displaced due to a damage occurred in the vertebral body. In order to treat the spondylolisthesis, surgery using a so-called anterior lumbar interbody fusion (ALIF) has been performed. Herein, as a conventional cage commonly used in the ALIF, a rectangular box-shaped cage is mainly used. In this case, since the rectangular box-shaped cage is formed to have a significantly longer lateral length than a longitudinal length, in order to insert it between the vertebrae, the surgical site should be largely exposed, and the disk should be cut in a large region. Therefore, there are problems of difficulty in the surgery and the process being very time-consuming.

In order to solve these problems, a lateral cage has been developed and used for intervertebral disc surgery (see Korean Patent Laid-Open Publication No. 10-2011-0013651). However, since such a lateral cage has a smaller surface area than the ALIF cage, the contacting area with the blood in the spinal cavity is decreased, such that a relatively long time is consumed for fusing the vertebrae, and thereby, a relatively long recovery time is required for the patient after surgery.

In addition, the lateral cage is provided with one end portion which is firstly inserted into the vertebra of the patient during surgery and has a height formed substantially the same as the other portions. Therefore, in order to insert the one end portion of the lateral cage between the vertebrae, there is a need to apply a great force, and even when being put under an anesthesia, the pain felt by the patient is large.

Meanwhile, Korean Patent Laid-Open Publication No. 10-2014-0018668 discloses a cage having a blade mounted and fixed between intervertebral disks, but this cage still entails the above-described problems due to a configurational limitation.

SUMMARY OF THE INVENTION

In consideration of the above-mentioned circumstances, it is an object of the present invention to provide an intervertebral fusion cage having an easy mountable shape while enlarging a contact area with blood in a spinal cavity during surgery.

In order to accomplish the above objects, according to one aspect of the present invention, there is provided an intervertebral fusion cage including: a front part; first and second side parts connected to both ends of the front part; and a rear part connected to the pair of first and second side parts, wherein the front part, the first and second side parts, and the rear part define fixing holes therein which are vertically opened, the first and second side parts are formed in a taper decreasing from the front part to the rear part, and a corner insertion part which is a portion connecting the rear part and the first side part has a smaller thickness than a portion connecting the rear part and the second side part.

Herein, at least one of a front corner part which faces the corner insertion part and connects the front part and the first side part, the front part, and the first side part may have a tool fastening part formed therein in a lateral direction.

In addition, the thickness of the first side part may be smaller than the thickness of the second side part.

Further, at least one of the front corner part which faces the corner insertion part and connects the front part and the second side part, the front part, and the first side part may have a flat seat surface in which the tool fastening part is formed.

Further, the space defined by the front part, the first and second side parts and the rear part may be divided into two or more fixing holes by a reinforcing part, and the fixing holes may have a cross-section area or shape different from each other.

Furthermore, a front corner part connecting the front part and the second side part may have a tool fastening part provided therein, the tool fastening part is formed in one end of a reinforcing tube disposed in the fixing holes between a corner insertion part and the front corner part facing the corner insertion part, the other end of the reinforcing tube contacts the corner insertion part, the corner insertion part has a first wedge seat into which a wedge is inserted, and a second wedge seat communicating with the first wedge seat, and a wedge is inserted in the first wedge seat, and by pressing the wedge through inside of the reinforcing tube, the wedge moves to the second wedge seat to be permanently fixed thereto, such that, a slit formed in the corner insertion part is expanded in a longitudinal direction thereof to increase an entire height of the corner insertion part in the longitudinal direction thereof.

The intervertebral fusion cage according to a first embodiment of the present invention is configured to be inserted between vertebrae from an anterior side and a lateral side, as well as an anterior lateral side while having the same surface area as the conventional ALIF cage, thereby it is possible to insert the intervertebral fusion cage by properly selecting an insert direction thereof by an operator as necessary.

Accordingly, since the vertebrae are fused with an enlarged contact area with blood in a spinal cavity within a relatively short time, the intervertebral fusion cage may be easily mounted on the vertebrae, while providing a significantly reduced recovery time for the patient.

In addition, the intervertebral fusion cage according to a second embodiment of the present invention is configured to be inserted between vertebrae only from the anterior lateral side, but by including a device for amending the height of the insertion portion so as to have the same height as the other portion, the insertion portion may contact with the vertebra surface to more decrease the fusing time compared to the intervertebral fusion cage according to the first embodiment of the present invention.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
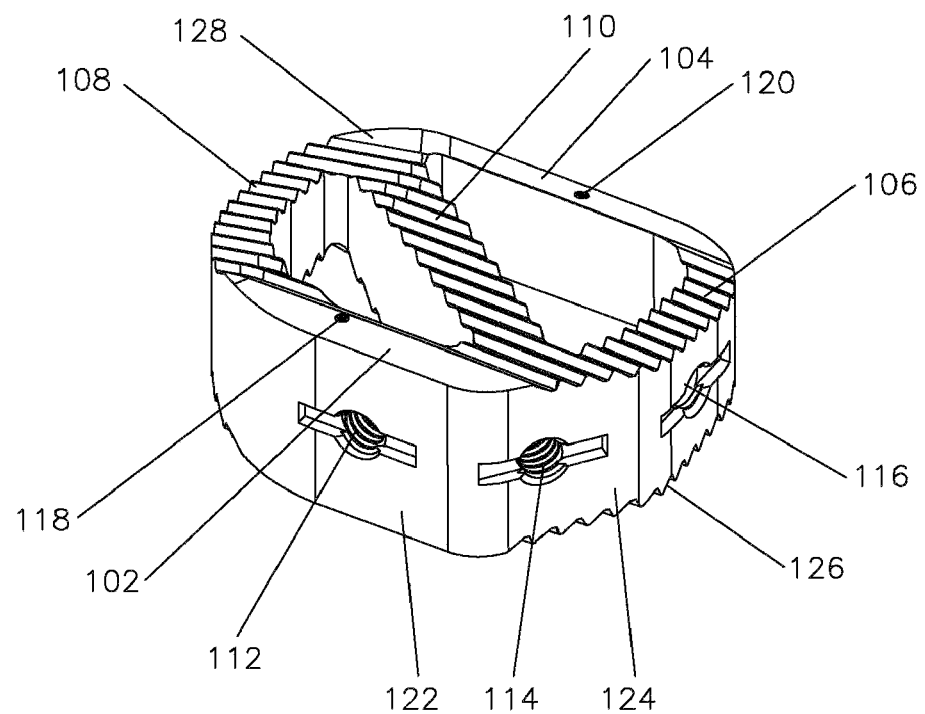
FIG. 1 is a perspective view illustrating an intervertebral fusion cage according to a first embodiment of the present invention as seen from a front thereof.

Hereinafter, the present invention will be described with reference to the accompanying drawings in detail. Referring to the drawings, wherein like reference characters designate like or corresponding parts throughout the several views. In the embodiments of the present invention, the publicly known functions and configurations that are judged to be able to make the purport of the present invention unnecessarily obscure will not be described.

The largest configurational characteristic of an intervertebral fusion cage according to the present invention is that: it has a taper of decreasing from a high anterior side when seen from a stomach of a human body to a low posterior side when seen from a back of the human body; and one end thereof on the posterior side has a smaller thickness than the other end, so as to be inserted between vertebrae from an anterior side and a lateral side, as well as an anterior lateral side, while basically having the shape similar to the conventional ALIF cage.

Hereinafter, intervertebral fusion cages 100 and 200 according to first and second embodiments of present invention having the above-described configurational characteristic will be described in detail with reference to FIGS. 1 to 8.

First, the intervertebral fusion cage 100 according to the first embodiment of present invention will be described in detail with reference to FIGS. 1 to 4.

The intervertebral fusion cage 100 generally includes a front part 102, first and second side parts 106 and 108 connected to both ends of the front part 102, and a rear part 104 connected to the pair of first and second side parts 106 and 108, wherein the front part 102, the first and second side parts 106 and 108 and the rear part 104 define fixing holes 130 and 132 therein which are vertically opened.

The intervertebral fusion cage 100 may be made of polymeric material which is harmless to a human body such as polyether ether ketone (PEEK), or formed by coupling a segment of such a polymeric material and a segment of metallic material with each other. Herein, the metallic material preferably uses titanium, stainless steel, or the like which is harmless to the human body.

The first and second side parts 106 and 108 are formed in a taper decreasing from the front part 102 to the rear part 104, and the front part 102, the first and second side parts 106 and 108 and the rear part 104 have protrusions formed on upper and lower surfaces thereof so as to prevent the intervertebral fusion cage 100 from sliding by contacting with the surface of the vertebra. Herein, the protrusions provided on the intervertebral fusion cage 100 according to the first embodiment of the present invention have a saw-toothed wedge shape which are substantially parallel to the front part 102 and disposed at a constant interval, but it is not limited thereto, and may have various shapes. By these wedge-shaped protrusions, the intervertebral fusion cage 100 may be easily inserted between the vertebrae, while preventing it from being separated therefrom.

In addition, inspection pins 118 and 120 are formed in the intervertebral fusion cage 100. The inspection pins 118 and 120 are used for, after the intervertebral fusion cage 100 is mounted between vertebrae, checking whether it is mounted at a correct position and alignment by X-ray irradiation. In the first embodiment of the present invention, two inspection pins 118 and 120 are used, but the number of the inspection pins 118 and 120 may be increased as necessary. On the other hand, the intervertebral fusion cage formed of the segment of metallic material as described above may not be provided with the inspection pin, or may use a smaller number of inspection pins than the intervertebral fusion cage made of polymeric material.

Figure 2:
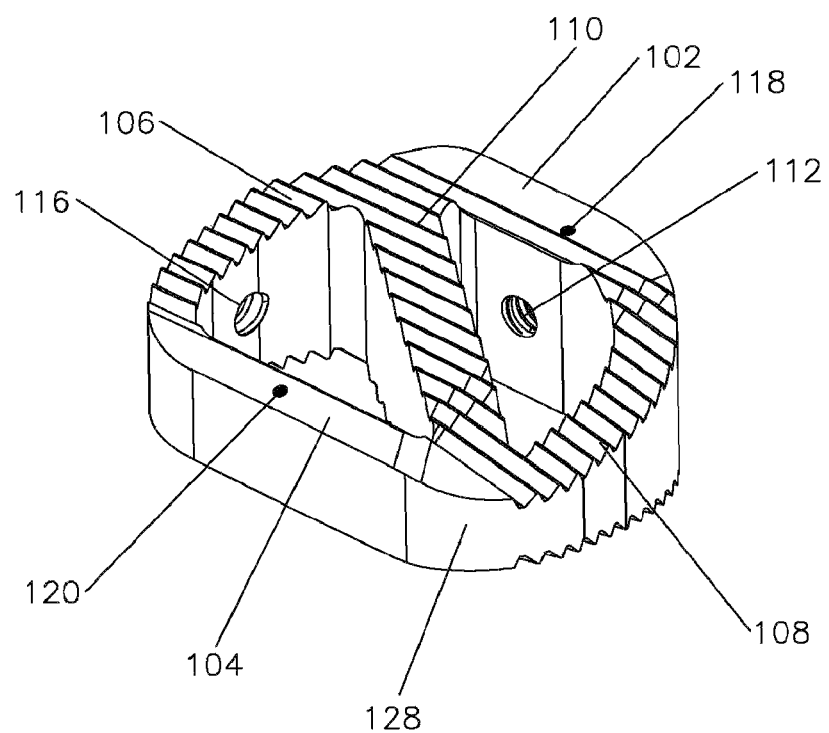
FIG. 2 is a perspective view of the intervertebral fusion cage illustrated in FIG. 1 as seen from a rear thereof.
Figure 3:
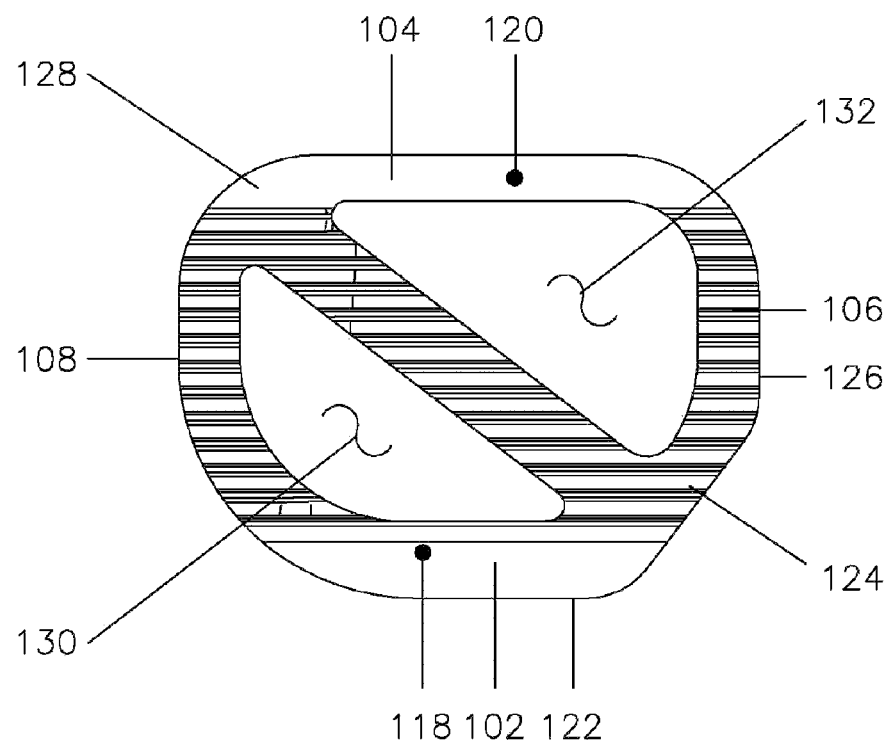
FIG. 3 is a plan view of the intervertebral fusion cage illustrated in FIG. 1.

Further, a corner insertion part 128 which is a portion connecting the rear part 104 and the first side part 106 has a smaller thickness than a portion connecting the rear part 104 and the second side part 106. In this case, the corner insertion part 128 is formed so as to be gradually decreased in thickness while forming a curved surface as illustrated in FIGS. 1 and 2, rather than decreased in a step shape. Thereby, the intervertebral fusion cage 100 may be mounted between the vertebrae by inserting the corner insertion part 128 into a space formed therebetween.

Additionally, in order to insert the intervertebral fusion cage 100 from the lateral side through a side of the human body, the first side part 108 is characterized in that it is formed so as to have a gradually reduced thickness in an outward direction. That is, the first side part 108 has a smaller thickness than the second side part 106. Thereby, the intervertebral fusion cage 100 may be further easily inserted from the lateral side due the shapes of the corner insertion part 128 and the second side part 106.

At least one of a front corner part which faces the corner insertion part 128 and connects the front part 102 and the first side part 108, the front part 102, and the first side part 108 has a tool fastening part 112, 114 or 116 formed therein in a lateral direction. The tool fastening parts 112, 114 and 116 may have female screws screwed with male screws formed on a mounting tool 20. In order to stably fix the flexible display unit 20, grooves are formed in the tool fastening parts 112, 114 and 116 around the female screws.

In addition, at least one front corner part which faces the corner insertion part 128 and connects the front part 102 and the second side part 106, the front part 102, and the first side part 108 has flat seat surfaces in which the tool fastening parts 112, 114 and 116 are formed. In particular, it is advantageous that the flat seat surfaces are formed around the female screws and the grooves of the tool fastening parts 112, 114 and 116 in terms of the stable coupling with the flexible display unit 20.

Further, a reinforcing part 110 may be provided in the fixing holes 130 and 132. The reinforcing part 110 is diagonally disposed in the fixing holes 130 and 132 between the corner insertion part 128 and the front corner part facing the corner insertion part 128. Furthermore, the reinforcing part 110 may be disposed so as to extend from the front part 102 to the rear part 104 or extend between the first side part 108 and second side part 106 facing with each other. Thereby, the space defined by the front part 102, the first and second side parts 106 and 108 and the rear part 104 is divided into the fixing holes 130 and 132 by the reinforcing part 110. The fixing holes 130 and 132 may have a cross-section area or shape different from each other, as necessary.

Figure 4:
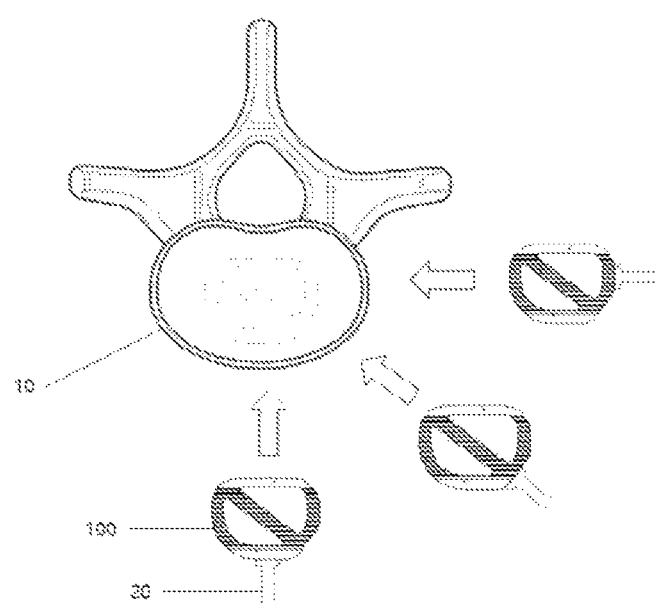
FIG. 4 is a schematic view illustrating a state of mounting the intervertebral fusion cage illustrated in FIG. 1 on a vertebra.

According to the first embodiment of the present invention, by the above-described configurational characteristics, it is possible to insert the intervertebral fusion cage 100 with the flexible display unit 20 between vertebrae 10 from any one of the anterior side, the lateral side and the anterior lateral side, as illustrated in FIG. 4. Thereby it is possible to insert the intervertebral fusion cage 100 by properly selecting the insert direction thereof by an operator as necessary.

Next, the intervertebral fusion cage 200 according to the second embodiment of the present invention will be described with reference to FIGS. 5 to 8. The intervertebral fusion cage 200 is formed so as to be inserted between vertebrae only from the anterior lateral side. The components of the second embodiment having the same configuration as the first embodiment will not be described.

The intervertebral fusion cage 200 generally includes a front part 202, first and second side parts 206 and 208 connected to both ends of the front part 202, and a rear part 204 connected to the pair of first and second side parts 206 and 208, wherein the front part 202, the first and second side parts 206, and 208 and the rear part 204 define fixing holes therein which are vertically opened.

The first and second side parts 206 and 208 are formed in a taper decreasing from the front part 202 to the rear part 204, and the front part 202, the first and second side parts 206, and 208 and the rear part 204 have protrusions formed on upper and lower surfaces thereof so as to prevent the intervertebral fusion cage 200 from sliding by contacting with the surface of the vertebra.

In addition, inspection pins 218 and 220 are formed in the intervertebral fusion cage 200. The inspection pins 218 and 220 are used for, after the intervertebral fusion cage 200 is mounted between vertebrae, checking whether it is mounted at a correct position and alignment by X-ray irradiation.

Figure 5:
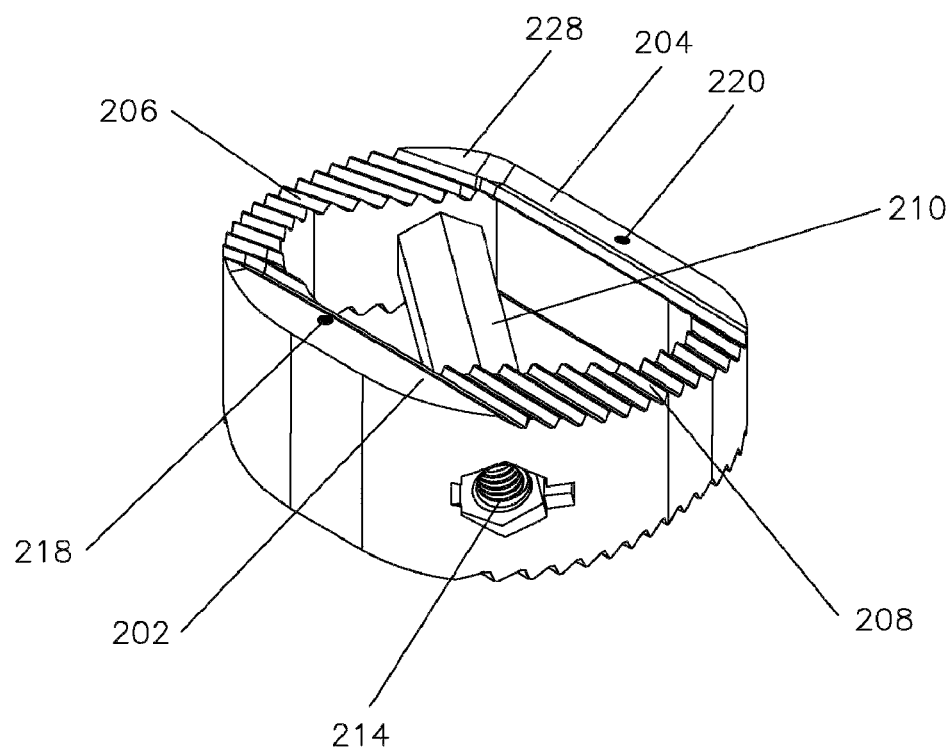
FIG. 5 is a perspective view illustrating an intervertebral fusion cage according to a second embodiment of the present invention as seen from the front thereof.
Figure 6:
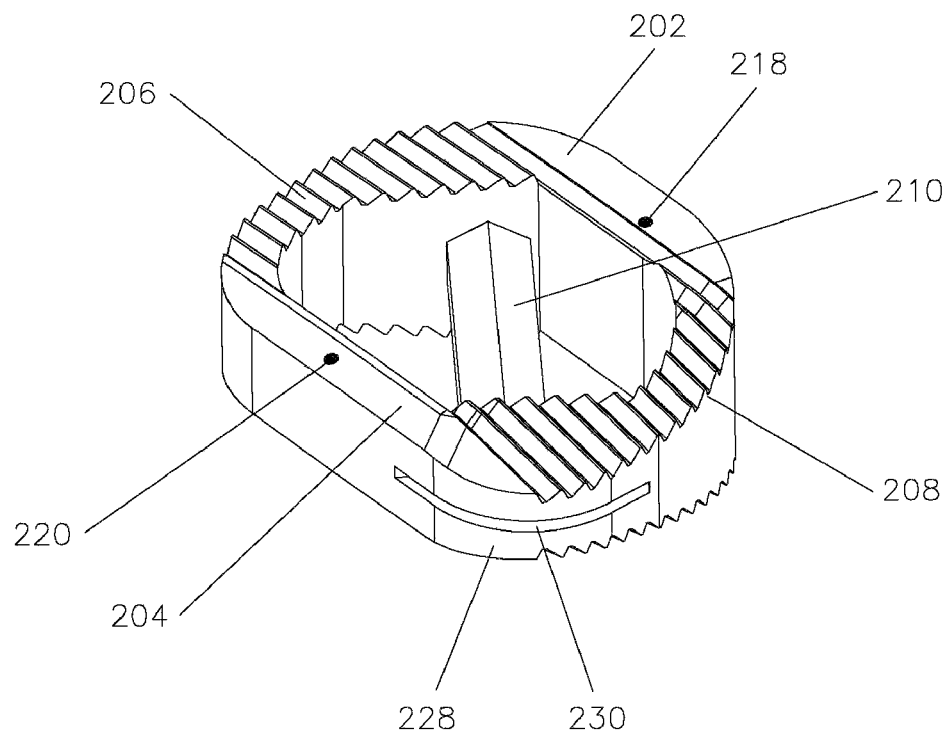
FIG. 6 is a perspective view of the intervertebral fusion cage illustrated in FIG. 5 as seen from the rear thereof.

Further, a corner insertion part 228 which is a portion connecting the rear part 204 and the first side part 208 has a smaller thickness than the portion connecting the rear part 204 and the second side part 206. In this case, the corner insertion part 228 is formed so as to be gradually decreased in thickness while forming a curved surface as illustrated in FIGS. 5 and 6, rather than decreased in a step shape. Thereby, the intervertebral fusion cage 200 may be mounted between the vertebrae by inserting the corner insertion part 228 into a space formed therebetween.

Additionally, in order to insert the intervertebral fusion cage 200 from the lateral side through a side of the human body, the first side part 208 is characterized in that it is formed so as to have a gradually reduced thickness in an outward direction. That is, the first side part 208 has a smaller thickness than the second side part 206. Thereby, the intervertebral fusion cage 200 may be further easily inserted from the lateral side due the shapes of the corner insertion part 228 and the second side part 206.

Tool fastening part 214 may be provided in a front corner part which faces the corner insertion part 228 and connects the front part 202 and the first side part 208. The tool fastening part 214 may have a female screw screwed with the male screw formed on the mounting tool 20. A flat seat surface may be formed on the front corner part around the tool fastening part 114 for stably coupling with the flexible display unit 20.

Further, a reinforcing tube 210 may be provided in the fixing holes corresponding to the fixing holes. The reinforcing tube 210 is diagonally disposed in the fixing holes between the corner insertion part 228 and the front corner part facing the corner insertion part 228. Thereby, the space defined by the front part 202, the first and second side parts 206, and 208 and the rear part 204 is divided into the fixing holes by the reinforcing tube 210. The cross-section area or shape of the fixing holes may be formed different from each other, as necessary.

The tool fastening part 214 may be integrally formed in one side of the reinforcing tube 210. In this case, the reinforcing tube 210 with a thread formed on one end thereof is inserted into the intervertebral fusion cage 200, such that the thread plays a role of the tool fastening part 214. Preferably, the reinforcing tube 210 has a polygonal shape so as not to rotate in the intervertebral fusion cage 200. In the second embodiment of the present invention, the reinforcing tube 210 has a hexagonal cross-section, for example.

The other end of the reinforcing tube 210 contacts the corner insertion part 228. In this case, the reinforcing tube 210 may be integrally coupled to the corner insertion part 228 to be fixed thereto.

Figure 7:
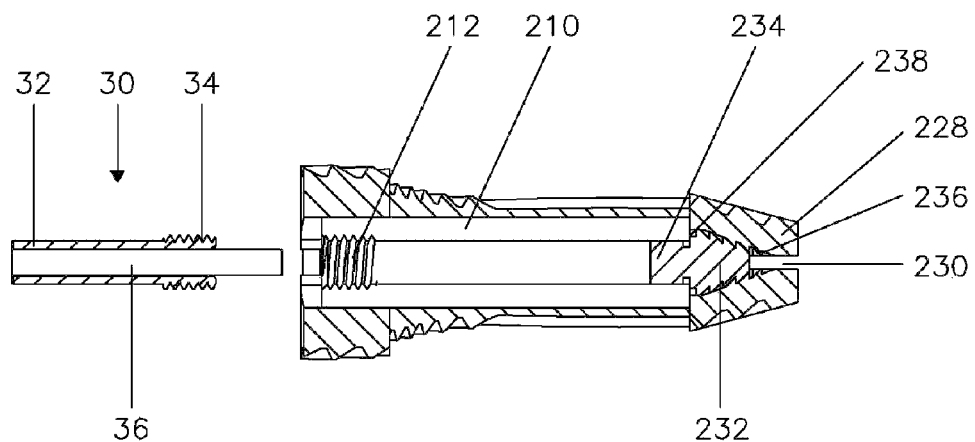
FIG. 7 is a cross-sectional view illustrating the intervertebral fusion cage illustrated in FIG. 5 and a mounting tool before fastening.
Figure 8:
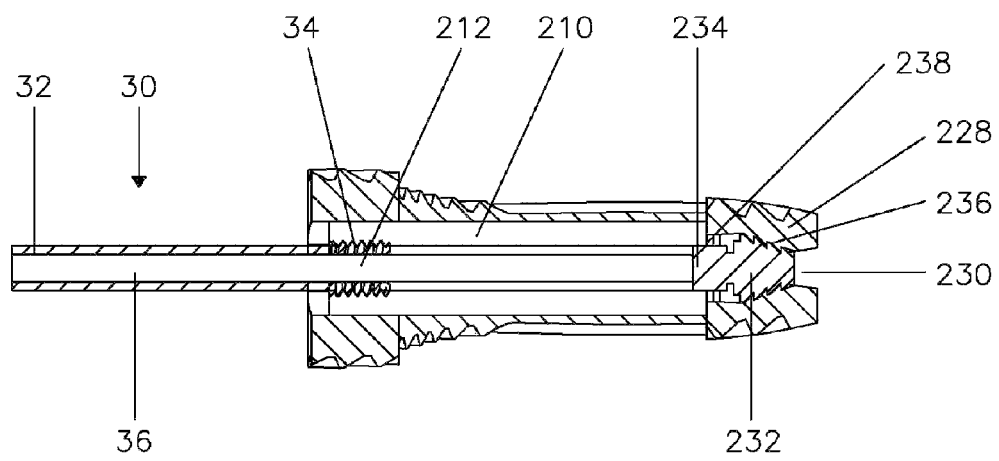
FIG. 8 is a cross-sectional view illustrating a state in which the mounting tool is fastened to the intervertebral fusion cage illustrated in FIG. 5, and a wedge is moved by using the mounting tool.

In addition, as illustrated in FIGS. 7 and 8, the corner insertion part 228 has a first wedge seat 238 into which a wedge 232 is inserted, and a second wedge seat 236 communicating with the first wedge seat 238, which are formed in one end thereof. The corner insertion part 228 has a slit 230 to be expanded within a predetermined range in a longitudinal direction thereof.

The reinforcing tube 210 has a longitudinal hole 212 into which a pressing rod 36 of a mounting tool 30 is inserted. Herein, the longitudinal hole 212 has a smaller inner diameter than the outer diameter of the wedge 232 so that the wedge 232 is not separated from the first wedge seat 238. In one end portion of the longitudinal hole 212, a wedge rod 234 to which the wedge 232 is fixed is slidably inserted.

As illustrated in FIG. 7, the first wedge seat 238, and in particular, the second wedge seat 236 has a rapidly changed cross-section, that is, rapidly reduced cross-section area to a right side in FIG. 7, such that the wedge 232 may be maintained in a state positioned in the first wedge seat 238. The mounting tool 30 has the pressing rod 36 integrally formed therein and a male screw 34 formed on one end portion of a mounting tube substrate 32, which is screwed with a female screw formed in the tool fastening part 214.

In addition, as illustrated in FIG. 8, by pressing the wedge 232 through an inside of the reinforcing tube 210, the wedge 232 moves to the second wedge seat 236 to be permanently fixed thereto. Therefore, the slit 230 is expanded in the longitudinal direction thereof, and thereby an entire height of the corner insertion part 228 in the longitudinal direction thereof may be increased.

More specifically, the intervertebral fusion cage 200 is inserted into the space between the vertebrae during surgery. Herein, the mounting screw 34 formed on the mounting tube substrate 32 of the mounting tool 30 is screwed with the female screw formed in the tool fastening part 214. In this state, a force is not applied to the pressing rod 36 inside of the mounting tube substrate 32 by an operator. Accordingly, the thickness of the corner insertion part 228 is smaller than the portion connecting the rear part 204 and the second side part 206.

When the intervertebral fusion cage 200 is inserted between the vertebrae, the wedge 234 of the wedge 232 is pressed by the pressing rod 36 toward the slit 230. As described above, the wedge 234 integrally formed with the wedge 232 is slidably inserted in the longitudinal hole 212 of the reinforcing tube 210. In variation, the wedge 232 may be directly pressed by the pressing rod 36 while eliminating the wedge 234. By the pressing, as illustrated in FIG. 8, the wedge 232 moves to the second wedge seat 236 to expand the slit 230, such that the entire height of the corner insertion part 228 in the longitudinal direction thereof may be increased. As a result, the corner insertion part 228 also contacts with the surface of the vertebra to enlarge the contact area with blood in the spinal cavity, such that the time consumed for fusing the vertebrae may be decreased, compared to the lenticular lens sheet 100 according to the first embodiment of the present invention.

While the present invention has been described with reference to the preferred embodiments, it will be understood by those skilled in the related art that various modifications and variations may be made therein without departing from the scope of the present invention as defined by the appended claims.

What is claimed is:

1. An intervertebral fusion cage comprising:
   a front part;
   first and second side parts connected to both ends of the front part; and
   a rear part connected to the pair of first and second side parts,
   wherein the front part, the first and second side parts, and the rear part define fixing holes therein which are vertically opened,
   the first and second side parts are formed in a taper decreasing from the front part to the rear part,
   a corner insertion part which is a portion connecting the rear part and the first side part has a smaller thickness than a portion connecting the rear part and the second side part,
   wherein a front corner part connecting the front part and the second side part has a tool fastening part provided therein,
   the tool fastening part is formed in one end of a reinforcing tube disposed in the fixing holes between a corner insertion part and the front corner part facing the corner insertion part,
   the other end of the reinforcing tube contacts the corner insertion part,
   the corner insertion part has a first wedge seat, and a second wedge seat communicating with the first wedge seat, and
   a wedge is inserted in the first wedge seat by pressing the wedge through inside of the reinforcing tube, the wedge moves to the second wedge seat to be permanently fixed thereto, such that, a slit formed in the corner insertion part that is expanded in a longitudinal direction thereof to increase an entire height of the corner insertion part in the longitudinal direction thereof.

2. The intervertebral fusion cage according to claim 1, wherein at least one of a front corner part, which faces the corner insertion part and connects the front part and the first side part, the front part, and the first side part has a tool fastening part formed therein in a lateral direction.

3. The intervertebral fusion cage according to claim 1, wherein a thickness of the first side part is smaller than a thickness of the second side part.

4. The intervertebral fusion cage according to claim 2, wherein at least one of the front corner part, which faces the corner insertion part and connects the front part and the second side part, the front part, and the first side part has a flat seat surface in which the tool fastening part is formed.

5. The intervertebral fusion cage according to claim 1, wherein a space is defined by the front part, the first and second side parts and the rear part and is divided into two or more fixing holes by a reinforcing part, and the fixing holes have a cross-section area or shape different from each other.

* * * * *